March 4, 1947. A. F. ETTER Plant Pat 724
CRAB APPLE TREE
Filed June 23, 1944
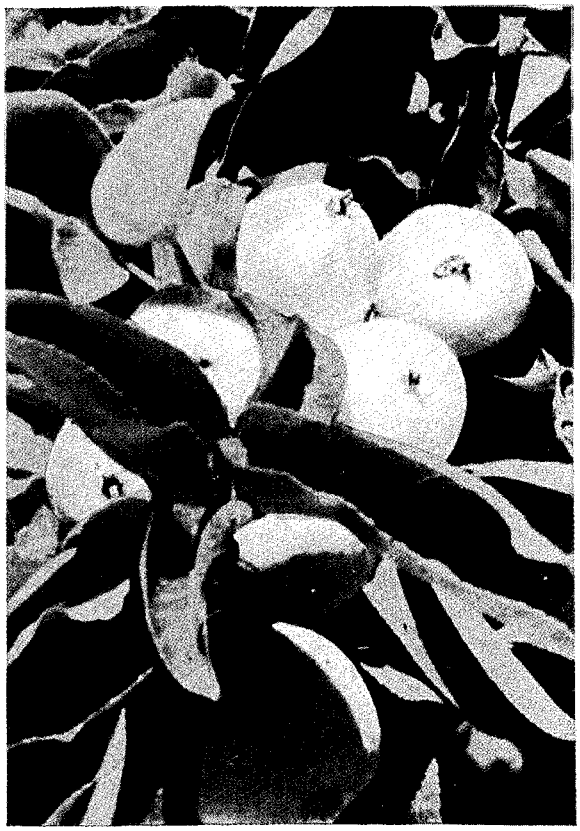
INVENTOR.
ALBERT F. ETTER.
BY
Chas. E. Townsend.
ATTORNEY.

Patented Mar. 4, 1947

Plant Pat. 724

UNITED STATES PATENT OFFICE

724

CRAB APPLE TREE

Albert F. Etter, Ettersburg, Calif., assignor to
George C. Roeding, Jr., Niles, Calif.

Application June 23, 1944, Serial No. 541,692

1 Claim. (Cl. 47—62)

This invention relates to a new variety of crab apple tree. The fruit of the new variety is comparable in size with the fruit of the Newtown-Spitzenberg crab and resembles the Transcendent crab.

The accompanying colored photograph illustrates this new discovery.

The following is a detail description of this new variety:

Shape: The fruit is oblong to conical.
Stem of fruit: Medium short.
Calyx: Closed.
Basin: Closed.
Skin: Medium tough, bright red striped, and solid over yellow undercolor.
Calyx tube: Medium large.
Core: Small; tender.
Seeds: Medium small; dark brown.
Flesh: Medium yellow, tender, rich in sugar, highly flavored, and juicy.

Foliage: Large, strong, healthy, and abundant.
Origin: The crab apple tree is a cross between the Newtown and Spitzenberg crab.

This diminutive apple surpasses most crab apples in color, form and flavor. Masses of brilliant red fruits almost conceal the foliage in fall. The flavor is sugary sweet. It is a good small apple for fresh eating. The tree chiefly resembles the Newtown and Spitzenberg crab in that it is characterized by producing fruit on one-year-old branches. The tree is a stronger grower than its parents and does not resemble any commonly known variety of apple or crab apple tree.

What I claim is:

A new variety of crab apple tree substantially as herein described characterized by the color, form, and flavor of its fruit, being brilliant red, oblong in shape, and sugary sweet, highly flavored, and juicy.

ALBERT F. ETTER.